US011890035B2

(12) United States Patent
Refai et al.

(10) Patent No.: US 11,890,035 B2
(45) Date of Patent: Feb. 6, 2024

(54) ARTICULATING ROD ASSEMBLY

(71) Applicant: REFAI TECHNOLOGIES, L.L.C., Atlanta, GA (US)

(72) Inventors: Daniel Refai, Atlanta, GA (US); Tyler Haskins, West Chester, PA (US)

(73) Assignee: REFAI TECHNOLOGIES, L.L.C., Atlanta, GA (US)

( * ) Notice: Subject to any disclaimer, the term of this patent is extended or adjusted under 35 U.S.C. 154(b) by 720 days.

(21) Appl. No.: 16/819,942

(22) Filed: Mar. 16, 2020

(65) Prior Publication Data

US 2020/0222084 A1 Jul. 16, 2020

Related U.S. Application Data

(63) Continuation of application No. 15/664,709, filed on Jul. 31, 2017, now Pat. No. 10,588,668, which is a continuation of application No. 14/110,491, filed as application No. PCT/US2012/032312 on Apr. 5, 2012, now Pat. No. 9,717,535.

(Continued)

(51) Int. Cl.
*A61B 17/70* (2006.01)

(52) U.S. Cl.
CPC .......... *A61B 17/704* (2013.01); *A61B 17/705* (2013.01); *A61B 17/7019* (2013.01); *A61B 17/7023* (2013.01); *A61B 17/7055* (2013.01)

(58) Field of Classification Search
CPC ............ A61B 17/7032; A61B 17/7034; A61B 17/7037; A61B 17/7038; A61B 17/7043; A61B 17/7044; A61B 17/7049; A61B 17/705; A61B 17/7055
See application file for complete search history.

(56) References Cited

U.S. PATENT DOCUMENTS 3,433,510 A   3/1969   Hulterstrum
5,800,435 A   9/1998   Errico
(Continued)

FOREIGN PATENT DOCUMENTS

EP   2158862   3/2010

OTHER PUBLICATIONS

International Search Report for PCT/US2012/032312, dated May 18, 2012, 5 pages.

(Continued)

*Primary Examiner* — Ellen C Hammond
(74) *Attorney, Agent, or Firm* — Heslin Rothenberg Farley & Mesiti PC; Jacquelyn A. Graff, Esq.

(57) ABSTRACT

An articulating assembly includes a first elongated element for attachment to a first anatomical region, and a second elongated element for attachment to a second anatomical region. In at least one embodiment, a coupling connects the first and second elongated elements. The coupling includes a moveable joint configured to allow polyaxial movement of the first elongated element with respect to the second elongated element. The assembly further includes a locking mechanism. The locking mechanism is operable in an unlocked condition to permit polyaxial movement of the first elongated element with respect to the second elongated element, and a locked condition to immobilize the movable joint and fix the position of the first elongated element with respect to the second elongated element.

14 Claims, 5 Drawing Sheets

Related U.S. Application Data

(60) Provisional application No. 61/473,342, filed on Apr. 8, 2011.

(56) References Cited

U.S. PATENT DOCUMENTS

| | | | |
|---|---|---|---|
| 7,695,500 | B2 | 4/2010 | Markworth |
| 7,901,433 | B2 | 3/2011 | Forton |
| 7,909,852 | B2 | 3/2011 | Boomer |
| 8,568,459 | B2 | 10/2013 | Uribe |
| 8,690,923 | B2 | 4/2014 | Lynch |
| 8,870,922 | B2 | 10/2014 | Hammer |
| 8,945,186 | B2 | 2/2015 | Walker |
| 2005/0288669 | A1* | 12/2005 | Abdou ............... A61B 17/7055 606/301 |
| 2007/0118121 | A1* | 5/2007 | Purcell ............... A61B 17/7055 606/276 |
| 2008/0243186 | A1* | 10/2008 | Abdou ............... A61B 17/7032 606/246 |
| 2009/0157120 | A1 | 6/2009 | Marino |
| 2010/0049252 | A1 | 2/2010 | Smisson, III |
| 2010/0234892 | A1 | 9/2010 | Mazda |
| 2012/0078306 | A1* | 3/2012 | Lynch ............... A61B 17/705 606/279 |
| 2012/0226316 | A1 | 9/2012 | Dant |

OTHER PUBLICATIONS

International Preliminary Report on Patentability and Written Opinion for PCT/US2012/032312, dated Oct. 8, 2013, pages.
EP Office Action for European Application No. 12714190.1, dated Oct. 22, 2014, 6 pages.
EP Office Action for European Application No. 12714190.1, dated Apr. 1, 2015, 5 pages.
EP Office Action for European Application No. 12714190.1, dated Aug. 2, 2016, 5 pages.

* cited by examiner

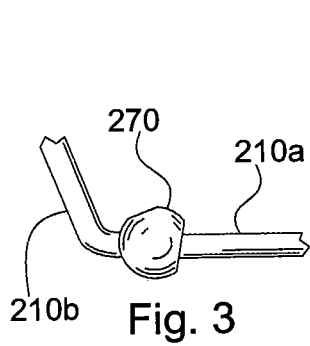
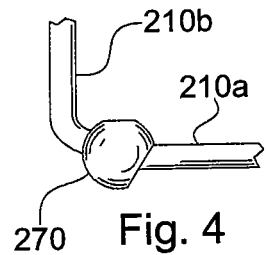
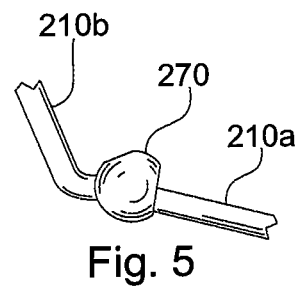
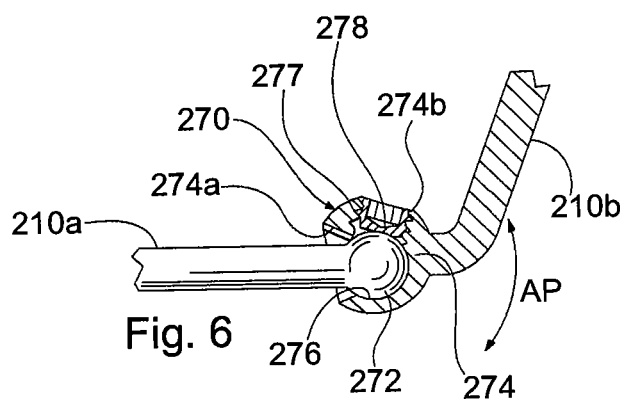
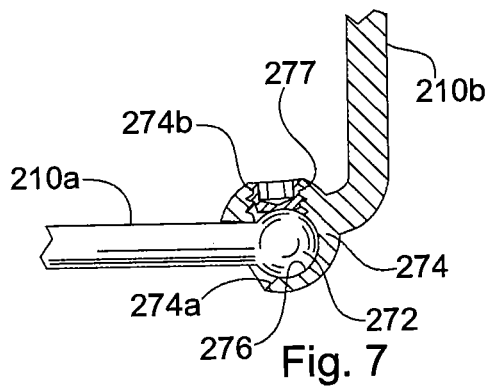
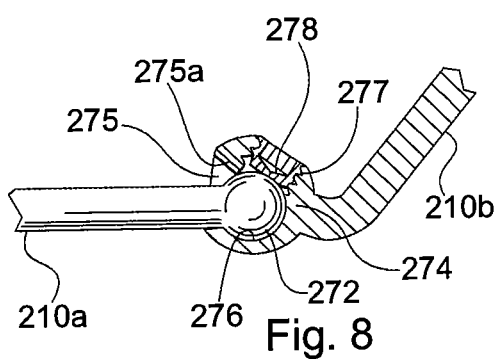
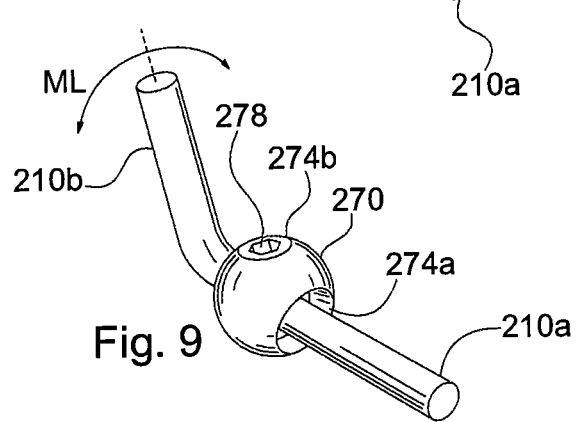

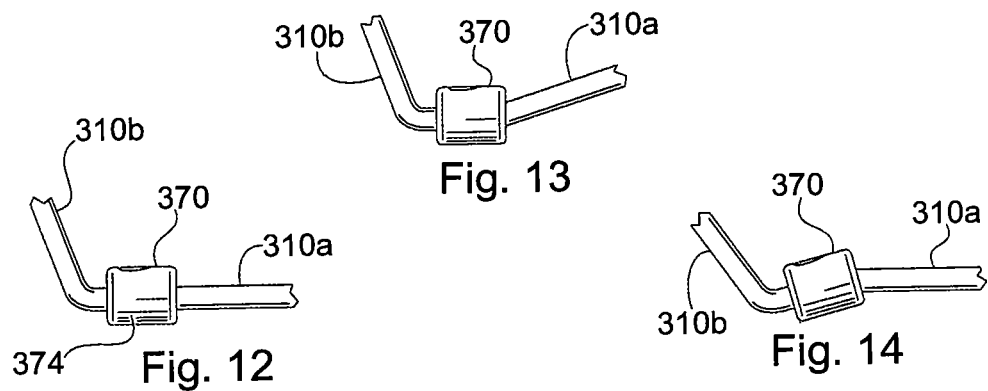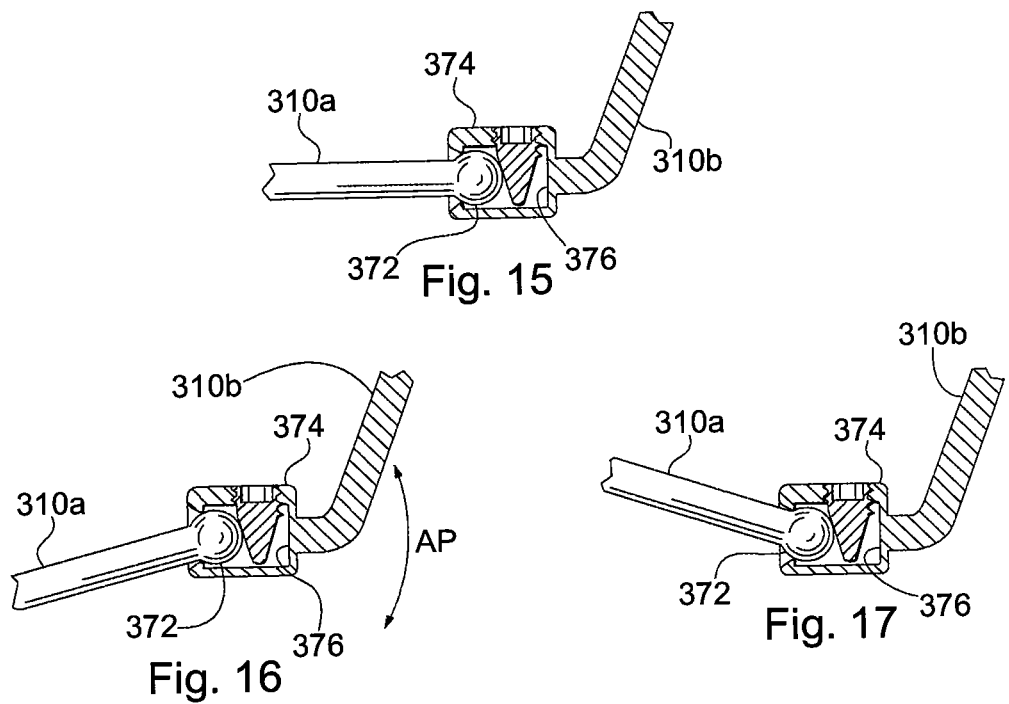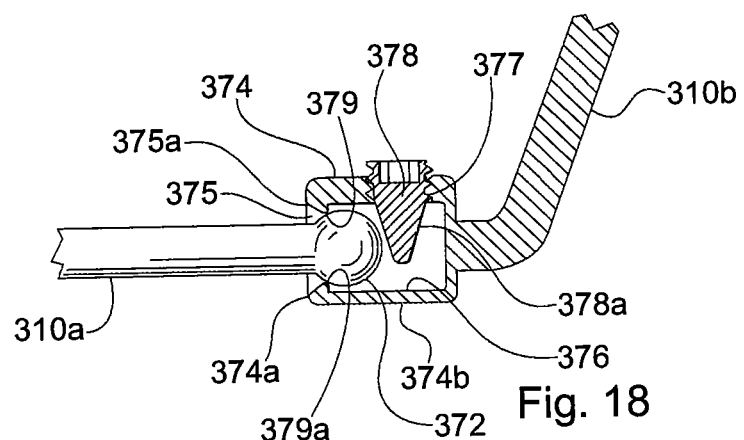

ARTICULATING ROD ASSEMBLY

RELATED APPLICATIONS

This application is a continuation of U.S. application Ser. No. 15/664,709 filed Jul. 31, 2017, which will issue as U.S. Pat. No. 10,588,668 on Mar. 17, 2020, which is a continuation of U.S. application Ser. No. 14/110,491 filed Apr. 3, 2014, which issued as U.S. Pat. No. 9,717,535 on Aug. 1, 2017, which is a National Phase application of International Application No. PCT/US2012/032312 filed Apr. 5, 2012 and published as WO 2012/138852 on Oct. 11, 2012, and which claims priority benefit under 35 U.S.C. § 119(e) of U.S. Provisional Application No. 61/473,342, filed Apr. 8, 2011, the contents of which are incorporated by reference herein in their entireties and for all purposes.

TECHNICAL FIELD

The present disclosure relates generally to surgical assemblies, and particularly to an articulating assembly that allows an elongated member to be angularly adjusted in multiple planes. The articulating assembly may be used, for example, to properly align fixation members with a patient's cervical vertebra and occipital region, or in a patient's lumbopelvic spine.

BACKGROUND

When performing posterior cervical stabilization, the surgeon typically places screws into the lateral mass of the cervical vertebral body followed by a titanium rod and set screws. This construct provides stabilization of the cervical spine to aid in fusion of one or more levels. Occasionally, one end section of the rod is anchored to a plate attached to the occipital region in a procedure called occipitocervical stabilization. In these constructs, the rod is characterized by two sections—a first section that extends over the cervical spine and a second section that connects to the occipital plate at an angle relative to the first section. One example of an occipitocervical fixation assembly 100 is shown in FIG. 1.

Fixation assembly 100 includes a pair of spinal rods 110. Each rod 110 is inserted into a series of screw assemblies 120 configured for anchoring into a vertebral body. Each screw assembly 120 includes a bone screw 130, a rod receiver 140, and a securing element 150 for locking one of the rods 110 into the rod receiver. Each rod 110 includes a first section 110a configured to extend over the cervical vertebrae and a second section 110b configured to attach to the patient's occipital region. The second sections 110b are anchored to an occipital plate 160 having two receivers 170 and two securing elements 180. Each rod 110 is bent to form an angle between its first section 110a and second section 110b.

In conventional occipitocervical fixation assemblies, the rod may be bent prior to placement to form the angle between the first and second sections. The pre-bent rod may be used to connect the screw or hook placed at C2 with the occipital plate. Alternatively, the screw or hook may be placed at C1 or C3. Because every patient has a different anatomy, one rod configuration will not suit all patients. Among other variables, the angle between the first and second rod sections will vary from patient to patient. Therefore, a pre-bent rod may not precisely match a patient's anatomy as the rod is placed. In many cases, the pre-bent rod requires further adjustment during placement, and must be bent intraoperatively.

Bending a rod prior to and during operation can be a time consuming and cumbersome process. In addition, bending the rod can create stress in the rod that decreases fatigue strength of the rod material. If fatigue strength is significantly reduced, the integrity of the rod can be compromised and pose a significant risk to the patient. The problems with rod bending are experienced not only with occipitocervical fixation assemblies, but are also experienced with lumbopelvic spine fixation assemblies, and other implant systems featuring elongated elements that must be manually configured to conform to specific spatial requirements.

SUMMARY

The drawbacks of conventional implant systems, and the practice of bending and shaping elongated elements, can be avoided with articulating assemblies in accordance with the invention.

Articulating assemblies in accordance with the invention may include an adjustable articulating assembly for implantation in a human or animal. The assembly may include a first elongated element for attachment to a first anatomical region, and a second elongated element for attachment to a second anatomical region. A coupling may connect the first and second elongated elements. The coupling may include a moveable joint configured to allow polyaxial movement of the first elongated element with respect to the second elongated element. The assembly may further include a locking mechanism. The locking mechanism may be operable in an unlocked condition to permit polyaxial movement of the first elongated element with respect to the second elongated element, and a locked condition to immobilize the movable joint and fix the position of the first elongated element with respect to the second elongated element.

BRIEF DESCRIPTION OF THE DRAWINGS

The foregoing summary and the following detailed description will be better understood in conjunction with the drawing figures, in which:

FIG. 3 is a truncated side view of components of the assembly in FIG. 2, shown in a first arrangement;

FIG. 4 is a truncated side view of components of the assembly in FIG. 2, shown in a second arrangement;

FIG. 5 is a truncated side view of components of the assembly in FIG. 2, shown in a third arrangement;

FIG. 6 is a truncated side view of components of the assembly in FIG. 2, shown in cross section in a fourth arrangement;

FIG. 7 is a truncated side view of components of the assembly in FIG. 2, shown in cross section in a fifth arrangement;

FIG. 8 is a truncated side view of components of the assembly in FIG. 2, shown in cross section in a sixth arrangement;

FIG. 9 is a truncated perspective view of components of the assembly in FIG. 2;

FIG. 12 is a truncated side view of components of the assembly in FIG. 11, shown in a first arrangement;

FIG. 13 is a truncated side view of components of the assembly in FIG. 11, shown in a second arrangement;

FIG. 14 is a truncated side view of components of the assembly in FIG. 11, shown in a third arrangement;

FIG. 15 is a truncated side view of components of the assembly in FIG. 11, shown in cross section in a first locked arrangement;

FIG. 16 is a truncated side view of components of the assembly in FIG. 11, shown in cross section in a second locked arrangement;

FIG. 17 is a truncated side view of components of the assembly in FIG. 11, shown in cross section in a third locked arrangement;

FIG. 18 is a side view of components of the assembly in FIG. 11, shown in cross section in an unlocked arrangement;

DETAILED DESCRIPTION OF EMBODIMENTS

Figure 1:
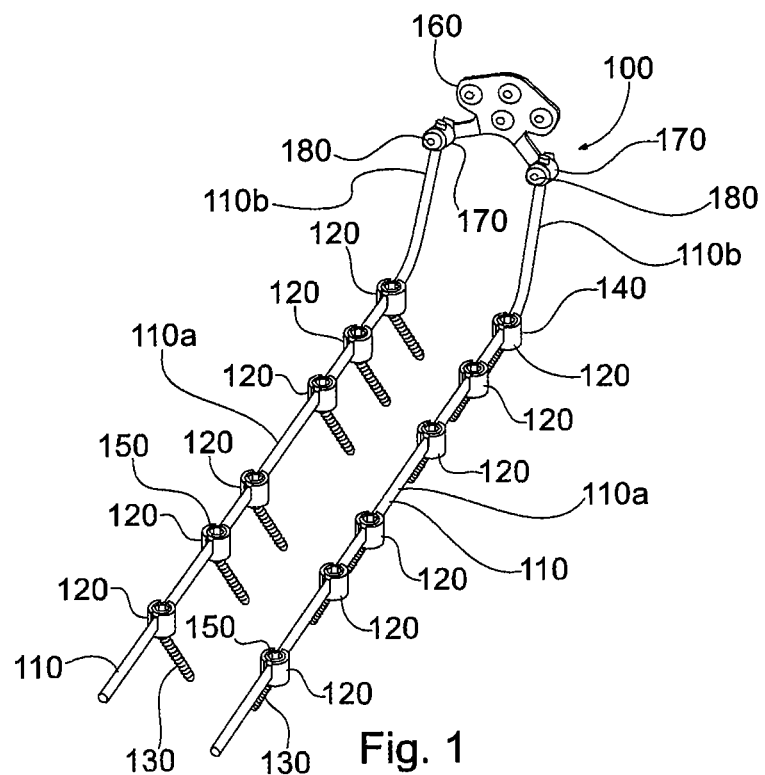
FIG. 1 is a perspective view of components of an occipitocervical stabilization system.

Although the invention is illustrated and described herein with reference to specific embodiments, the invention is not intended to be limited to the embodiments shown. Various modifications may be made in the details within the scope and range of equivalents of the claims and without departing from the invention.

Assemblies in accordance with the invention may include an adjustable articulating assembly for implantation in a human or animal. The adjustable articulation assembly may include a first elongated element for attachment to a first anatomical region, and a second elongated element for attachment to a second anatomical region. The assembly may also include a coupling connecting the first elongated element with the second elongated element. The coupling may include a moveable joint configured to allow polyaxial movement of the first elongated element with respect to the second elongated element. The coupling may also include a locking mechanism. The locking mechanism may be operable in an unlocked condition to permit polyaxial movement of the first elongated element with respect to the second elongated element. The locking mechanism may also be operable in a locked condition to immobilize the movable joint and fix the position of the first elongated element with respect to the second elongated element.

The assembly may include a moveable joint that includes a ball and socket joint. The ball and socket joint may include a spherical end on at least one of the first elongated element and the second elongated element. The first elongated element may be movable through an angle of at least about 20° relative to the second elongated element.

The locking mechanism may include at least one screw. The screw may include a tapered wedge portion. The screw may directly engage one of the first and second elongated elements when the locking mechanism is in the locked condition.

The moveable joint may feature a hollow receptacle. The hollow receptacle may be generally spherical. Alternatively, the hollow receptacle may be generally cylindrical. The hollow receptacle may include at least one open end. The open end may form an enlarged opening that passes into the hollow receptacle. The enlarged opening may include a tapered edge that tapers outwardly. The hollow receptacle may include at least one annular seat. The annular seat projects inwardly into a socket in the hollow receptacle.

The at least one annular seat may form a constricted opening having a first diameter. One of the first and second elongated elements may include a ball end disposed in the hollow receptacle, the ball end having a second diameter larger than the first diameter. The ball end may be compressed against the seat when the locking mechanism is in the locked condition.

The first and second elongated elements may be associated with assemblies that are implanted in various areas of a human or animal. For example, the first and second elongated elements may be associated with rod implants. The first and second elongated elements may include sections of an occipital spine fusion rod. Alternatively, the first and second elongated elements may include sections of a lumbar spine fusion rod. This description will now discuss embodiments that feature rods, with the understanding that assemblies in accordance with the invention can be used with other elongated elements.

Applicants have developed an articulating fixation assembly that allows the rod's angle to be easily adjusted in multiple planes. Angular adjustment is done by moving an articulating joint between the first and second sections, as opposed to bending the rod. The articulating joint simplifies the task of adjusting the rod angle, and creates no stress in the rod material. By adjusting the rod angle in multiple planes, the rod can be adjusted to not only match the patient's anatomy, but also meet additional spatial requirements necessitated by other components of the assembly or instrumentation.

Figure 2:
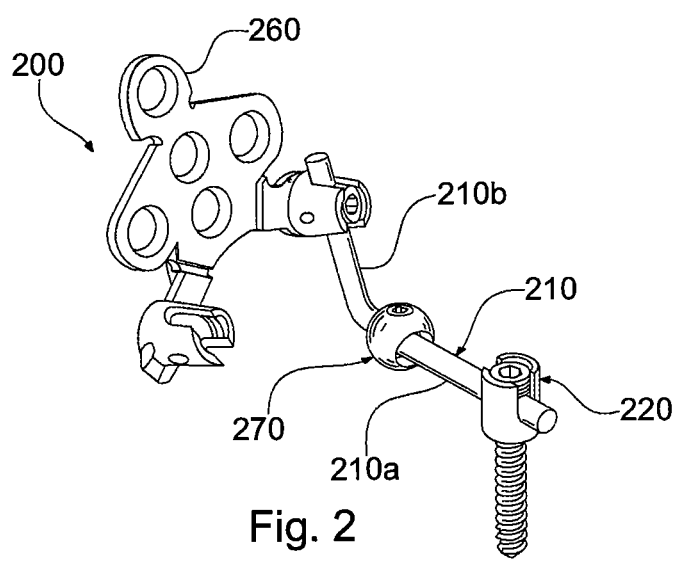
FIG. 2 is a truncated perspective view of an articulating fixation assembly in accordance with one embodiment.
Figure 10:
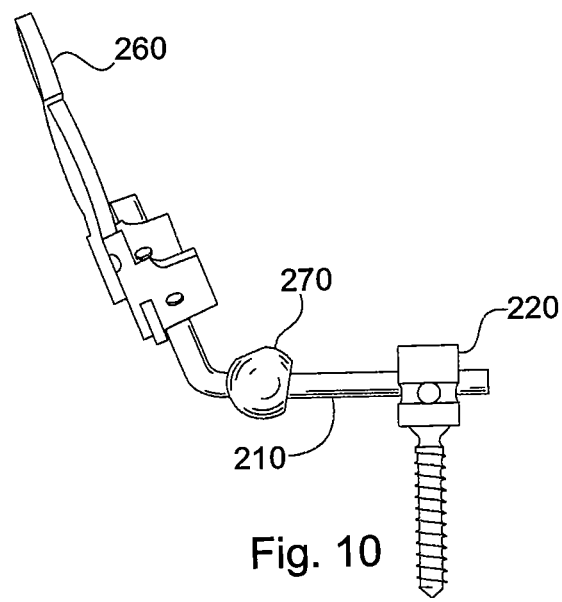
FIG. 10 is a truncated side view of components of the assembly in FIG. 2.

Referring now to FIGS. 2-10, an articulating fixation assembly 200 is shown in accordance with a first exemplary embodiment. Assembly 200 includes two rods 210, one of which is shown, and one of which is not shown for clarity. Rod 210 includes a first section 210a, a second section 210b and a coupling 270 that interconnects the first and second sections together. First section 210a, which is truncated for clarity, is secured to a screw assembly 220. Second section 210b is connected to an occipital plate 260. It will be understood that first section 210a may be longer and connect with multiple anchors, like hooks or additional screw assemblies. In addition, it will be understood that assembly 200 includes two rods 210 that may be configured identically or differently.

FIGS. 6-8 illustrate how coupling 270 can be used to adjust the angulation between the first and second sections 210a and 210b. Coupling 270 is formed by a ball and socket joint. Specifically, coupling 270 includes a spherical ball end 272 on one end of first section 210a Coupling 270 further includes a receptacle 274 on one end of the second section 210b Receptacle 274 includes a rounded socket 276 adapted to receive ball end 272 inside the receptacle. Ball end 272 and socket 276 form the ball and socket joint that allows the first section 210a of rod 210 to move polyaxially with respect to the second section 210b. As used herein, the term "polyaxial" or "polyaxially" refers to the ability of a first element to pivot in multiple planes with respect to a second element to which the first element is coupled. First section 210a can move polyaxially with respect to second section 210b, and vice versa, so that the two sections can pivot in multiple planes with respect to one another. In this arrangement, second section 210b can pivot with respect to first section 210a in an anterior-posterior plane shown by arrows AP in FIG. 6, and a medial-lateral plane shown by arrows ML in FIG. 9.

Receptacle 274 has a generally spherical shape with two flattened sections 274a and 274b. Flattened section 274a lies adjacent to an enlarged opening 275 that passes through the receptacle 274 and into the socket 276. Enlarged opening 275 has a tapered edge 275a and a diameter that increases as the tapered edge extends outwardly and away from the center of receptacle 274. As such, tapered edge 275a forms a frustoconical surface around enlarged opening 275. Enlarged opening 275 and tapered edge 275a allow first section 210a to pivot polyaxially through a wide range of motion relative to second section 210b.

Flattened section 274b includes a passage 277 and a locking screw 278 in the passage. Locking screw 278 includes an external thread that engages an internal thread in passage 277. As such, locking screw 278 is movable in passage 277 by threading the screw into the passage and axially rotating the screw. Passage 277 extends into rounded socket 276. Locking screw 278 is movable in passage 277 between a locked position and an unlocked position. In the locked position, locking screw 278 is positioned in passage 277 and extends into rounded socket 276 to engage ball end 272. When locking screw 278 engages ball end 272 in the locked position, the locking screw compresses the ball end in the socket 276. In this compressed condition, frictional forces between ball end 272, screw 278 and the socket wall 276 immobilize the ball end and prevent it from pivoting, so that the first section 210a of rod 210 is locked in position relative to second section 210b. In the unlocked position, locking screw 278 is positioned in passage 277 out of contact with ball end 272, leaving the ball end free to move in socket 276. This allows first section 210a to pivot polyaxially relative to second section 210b.

Figure 11:
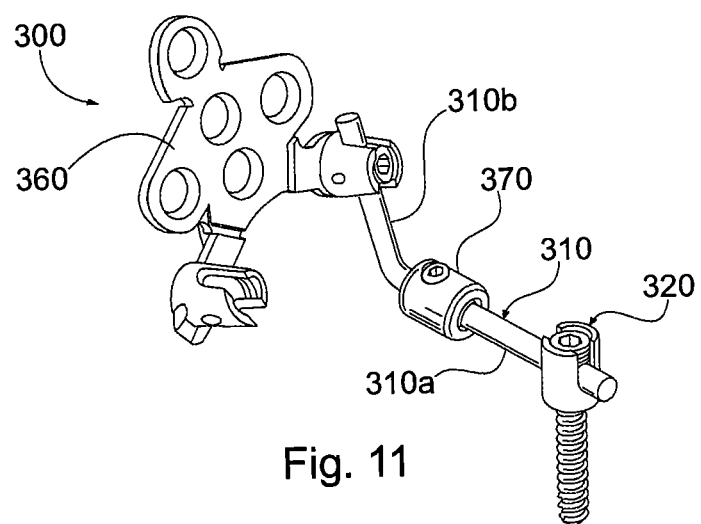
FIG. 11 is a truncated perspective view of an articulating fixation assembly in accordance with another embodiment.
Figure 19:
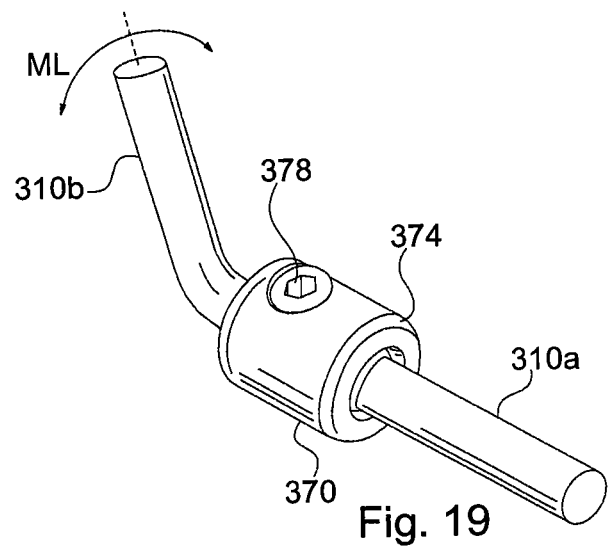
FIG. 19 is a truncated perspective view of components of the assembly in FIG. 11.
Figure 20:
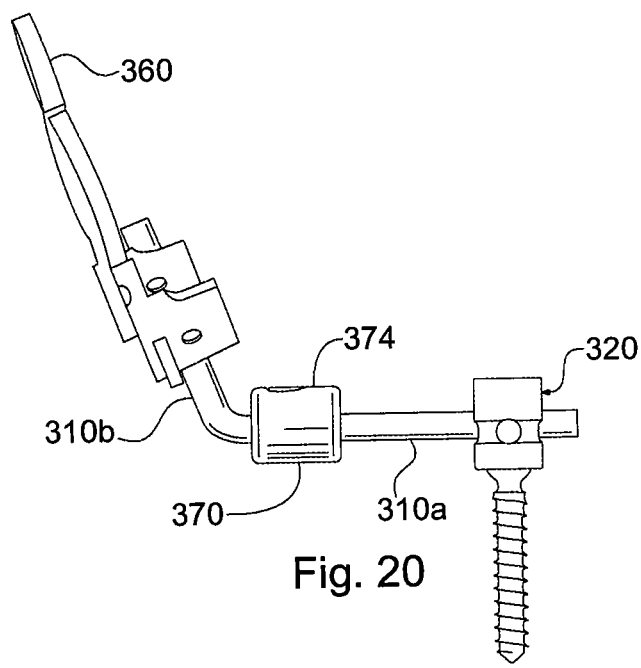
FIG. 20 is a truncated side view of the assembly in FIG. 11.

FIGS. 11-20 illustrate an articulating fixation assembly 300 shown in accordance with a second exemplary embodiment. Assembly 300 includes two rods 310, one of which is shown, and one which is not shown for clarity. Rod 310 includes a first section 310a, a second section 310b and a coupling 370 that interconnects the first and second sections together. First section 310a, which is truncated for clarity, is secured to a screw assembly 320. Second section 310b is connected to an occipital plate 360. It will be understood that first section 310a may be longer and connect with multiple anchors, like hooks or additional screw assemblies. In addition, it will be understood that assembly 300 includes two rods 310 that may be configured identically or differently.

FIGS. 15-17 illustrate how coupling 370 can be used to adjust the angulation between the first and second sections 310a and 310b. Coupling 370 includes a spherical ball end 372 on one end of first section 310a. Coupling further includes a receptacle 374 on one end of the second section 310b. Receptacle 374 includes a cylindrical socket 376 adapted to receive ball end 372 inside the receptacle. Ball end 372 and socket 376 form the ball and socket joint that allows the first section 310a of rod 310 to move polyaxially with respect to the second section 310b. First section 310a and second section 310b can pivot in multiple planes with respect to one another. In this arrangement, second section 310b can pivot with respect to first section 310a in an anterior-posterior plane shown by arrows AP in FIG. 16, and a medial-lateral plane shown by arrows ML in FIG. 19.

Receptacle 374 has a generally cylindrical body 374b with one open end 374a. Open end 374a has an enlarged opening 375 that passes through the receptacle wall and into the socket 376. Enlarged opening 375 has a tapered edge 375a that tapers outwardly, allowing first section 310a to pivot polyaxially through a wide range of motion relative to second section 310b. Receptacle 374 further includes an annular seat 379 that projects radially inwardly into socket 376 as shown, just inside open end 374a. Seat 379 forms a constricted opening 379a having a diameter less than the diameter of ball end 372. In this arrangement, seat 379 prevents ball end 372 from exiting socket 376. Ball end 372 rests against seat 379 is slidable engagement, while being captively contained in socket 376.

Body 374b includes a passage 377 that connects with socket 376. A locking screw 378 is contained in the passage. Locking screw 378 includes an external thread that engages an internal thread in passage 377. As such, locking screw 378 is movable in passage 377 by threading the screw into the passage and axially rotating the screw. Locking screw 378 also includes a tapered shaft or wedge portion 378a that extends into socket 376.

Locking screw 378 is movable in passage 377 between a locked position and an unlocked position. In the locked position, wedge portion 378a of locking screw 378 extends into socket 376 and engages ball end 372. When locking screw 378 engages ball end 372 in the locked position, the locking screw compresses or wedges the ball end against seat 379, trapping the ball end between the wedge portion 378a and seat. In this trapped condition, frictional forces between ball end 372 and seat 379, and frictional forces between the ball end and wedge portion 378a, immobilize the ball end and prevent it from pivoting relative to socket 376. As such, first section 310a of rod 310 is locked in position relative to second section 310b. In the unlocked position, locking screw 378 is positioned in passage 377 with wedge portion 378a out of contact with ball end 372. This leaves ball end 372 free to move in socket 376, so that first section 310a can pivot polyaxially relative to second section 310b. FIGS. 15-17 show three different arrangements, each in a locked condition. FIG. 18 shows an arrangement in an unlocked condition.

The embodiments described thus far provide the benefit of a smooth articulating connection between first and second elongated elements. The connection allows multi-planar rotation that permits angular adjustment of the rod sections not only in the anterior-posterior plane but also the medial-lateral direction. Preferably, the connections in either embodiment provide about 20° of motion in each allowable direction (40° total through a given plane). A smaller or larger range of motion in one or more directions may be desirable in certain cases, and are therefore also contemplated. For example, the connections may permit a maximum of about 10° of motion in any allowable direction, or a maximum of about 15° of motion in any allowable direction. Or, the connections may permit a maximum of about 25° of motion in any allowable direction, or a maximum of about 30° of motion in any allowable direction.

The range of motion for a specific coupling may be controlled by the size and shape of the openings in the receptacles, through which the rod sections extend. For example, the size and shape of opening 375 may be customized to permit different ranges of motion in different planes. Where it is desired to have a larger range of motion in one plane, and a smaller range of motion in another plane, the opening through which the rod section extends may be elliptical in shape, with the major axis (or widest dimension) of the elliptical opening aligned with the plane to receive the largest range of motion. Various openings having symmetrical and asymmetrical shapes may be used to control the range of pivot motion of the rod sections.

The embodiments that have been described thus far provide examples of articulating assemblies that permit angulation of rod sections in multiple planes. The foregoing examples do not represent the only possible arrangements that are contemplated. The features of one embodiment may be added to or substituted for features in another embodiment. Numerous variations, changes and substitutions will occur to those skilled in the art without departing from the principles described herein.

For example, an articulating rod assembly may include a receptacle with two or more locking elements that are advanced into the socket to lock the ball end in a locking position. The locking elements may be set screws with or without tapered wedge portions that engage the ball end. Alternatively, the locking elements can be non-threaded elements, such as a simple shim which is physically pushed into the socket against the ball end to prevent the ball end from pivoting in the socket. The locking elements may be removable from the receptacle, or captively contained in the wall of the receptacle.

Articulating rod assemblies in accordance with the invention may also include multiple ball and socket joints within a single coupling. In one embodiment, the coupling is a cylindrical coupling with a spherical socket at each end. Each rod section includes a ball end, like first elongated element 310a in FIG. 15. Each ball end is disposed in one of the sockets, forming two ball and socket joints positioned at opposite ends of the cylindrical coupling. The ball and socket joints allow both rod sections to move polyaxially with respect to the cylindrical coupling, and to one another. A pair of locking mechanisms, such as set screws, extend through a wall of the cylindrical coupling. Each set screw is used to lock and unlock one of the ball and socket joints.

The receptacles may have various inner and outer geometries. Moreover, the receptacles may include one or more finger tabs or other external features that allow a surgeon to easily grip and pivot the coupling. The body of the receptacle and rods may include markings or indicia to assist the surgeon in monitoring, measuring or approximating the angular adjustments being made between the rod sections.

While the embodiments presented thus far are described in use with occipitocervical fixation assemblies, articulating assemblies in accordance with the invention may be used in a variety of applications. For example, an articulating assembly can be used to interconnect first and second rod sections that are implanted in the lumbar region of the spine. The first and second rod sections may be arranged in an offset configuration, with the articulating coupling providing the desired offset between the rod sections.

Articulation assemblies in accordance with the invention can also be used in a rod to rod connector construct. The articulating assembly can connect an existing fusion construct with another, to treat scoliosis or adjacent segment disease. A new rod fixation system can be connected to an existing rod using the articulating assembly.

Articulating assemblies in accordance with the invention may also be used in a variety of applications outside of spine surgery, including any applications where elongated members are connected to one another, or to other structures. It should be understood that assemblies in accordance with the invention need not be used with rods, as noted above. Assemblies in accordance with the invention may feature elongated elements in the form of elongated plates, shafts, or any type of elongated body member.

All such variations are contemplated as part of this disclosure and covered by the appended claims.

The invention claimed is:

1. An adjustable articulating spinal rod assembly, the assembly comprising:
   a first rod for attachment to a first anatomical region;
   a second rod for attachment to a second anatomical region; and
   at least one coupling member connecting the first rod with the second rod, the at least one coupling member comprising:
      a body having a first opening and a second opening, wherein the first opening is at a first end of the body and the second opening near a second end of the body; and
      at least one locking mechanism received within the second opening, wherein the at least one locking mechanism has a conical shape and wherein the conical shape of the at least one locking mechanism directly engages an end of the first rod;
   wherein the at least one coupling member is positioned between the first rod and the second rod and moveably couples the first rod and the second rod.

2. The assembly of claim 1, wherein a first end of the first rod is arcuate shaped.

3. The assembly of claim 1, wherein the first rod is movable through an angle of at least about 20° relative to the second rod.

4. The assembly of claim 1, wherein the at least one locking mechanism is two locking mechanisms.

5. The assembly of claim 4, wherein the two locking mechanisms are two threaded set screws.

6. The assembly of claim 1, wherein the body comprises an outer surface and is generally cylindrically shaped.

7. The assembly of claim 6, wherein the outer surface has one or more tabs extending outward from the outer surface.

8. The assembly of claim 6, wherein the outer surface has at least one marking or indicia for measuring angular adjustments between the first rod and the second rod.

9. The assembly of claim 1, further comprising a third rod and a fourth rod, wherein the third rod and the fourth rod are parallel to the first rod and the second rod when the assembly is implanted in a spine.

10. The assembly of claim 9, wherein the first rod and the third rod are connected to a plate member, wherein the plate member is configured to be attached to a human skull.

11. The assembly of claim 9, wherein the first rod and the second rod further comprises:
   at least one screw assembly, wherein the at least one screw assembly comprises:
      a bone screw;
      a rod receiver; and
      a securing element, wherein the rod receiver has a channel through which at least one of the first rod and the second rod pass.

12. The assembly of claim 11, wherein the at least one screw assembly is moveable along a length of the first rod, the second rod, the third rod and the fourth rod to attach the first rod to the first anatomical region, to attach the second rod to the second anatomical region, to attach the third rod to a third anatomical region and to attach the fourth rod to a fourth anatomical region.

13. The assembly of claim 1, wherein the at least one locking mechanism comprises:
   a head with an external thread; and
   a tapered shaft extending away from a bottom surface of the head,
   wherein the locking mechanism is monolithic.

14. An adjustable articulating spinal rod assembly, the assembly comprising:
   a first rod for attachment to a first anatomical region;
   a second rod for attachment to a second anatomical region; and at least one coupling member connecting the first rod with the second rod, the at least one coupling member comprising:
- a body having a first opening and a second opening, wherein the first opening is at a first end of the body and the second opening near a second end of the body; and
- at least one locking mechanism received within the second opening, wherein the at least one locking mechanism has a conical shape and engages an end of the first rod, and wherein the at least one locking mechanism further comprises:
  - a head with an external thread; and
  - a tapered shaft extending away from a bottom surface of the head, wherein the locking mechanism is monolithic;

wherein the at least one coupling member is positioned between the first rod and the second rod and moveably couples the first rod and the second rod.

* * * * *